United States Patent [19]

Barenholz et al.

[11] Patent Number: 5,622,715
[45] Date of Patent: Apr. 22, 1997

[54] METHOD OF IMPROVING RENAL FUNCTION

[75] Inventors: Yechezkel Barenholz; Ziv Greenfeld, both of Jerusalem, Israel

[73] Assignee: Yissum Research Development Company of the Hebrew University of Jerusalem, Jerusalem, Israel

[21] Appl. No.: 628,970

[22] Filed: Apr. 8, 1996

Related U.S. Application Data

[63] Continuation of Ser. No. 257,865, Jun. 10, 1994, abandoned.

[51] Int. Cl.$^6$ .......................... A61K 9/127; A61K 9/133
[52] U.S. Cl. ............................................................. 424/450
[58] Field of Search ........................ 424/450; 428/402.2

[56] References Cited

U.S. PATENT DOCUMENTS

| | | | |
|---|---|---|---|
| 4,252,793 | 2/1981 | Altman | 424/199 |
| 4,308,166 | 12/1981 | Marchetti et al. | 262/316 |
| 4,310,505 | 1/1982 | Baldeschwieler et al. | 424/1 |
| 4,544,545 | 10/1985 | Ryan et al. | 424/1.1 |
| 4,812,314 | 3/1989 | Barenholz et al. | 424/450 |
| 5,273,961 | 12/1993 | Clark | 514/8 |

FOREIGN PATENT DOCUMENTS

| | | |
|---|---|---|
| 0050793 | 5/1982 | European Pat. Off. . |
| 2089681 | 6/1982 | United Kingdom . |
| WO86/00238 | 1/1986 | WIPO . |
| 86/01102 | 2/1986 | WIPO . |

OTHER PUBLICATIONS

Almog, S., et al., "States of aggregation and phase transformations in mixtures of phosphatidylcholine and octyl gluco-side," Abstract Only from *Biochemistry* 29(19): 4582–4592 (1990).

Barenholz, Y., et al., "A Simple Method for the Preparation of Homogeneous Phospholipid Vesicles," *Biochemistry* 16(12): 2806–2810 (1977).

Barenholz, Y., "Sphingomyelin–Lecithin Balance in Membranes: Composition, Structure, and Function Reletionships," Chapter 5 from *Physiology of Membrane Fluidity*, vol. 1 (Shinitzky, M., ed., CRC Press, Inc., Florida, 1984, pp. 131–173).

Barenholz, Y., and T.E. Thompson, "Sphingomyelines in Bilayers and Biological Membranes," *Biochemica et Biophysica Acta* 604: 129–158 (1980).

Barenholz, Y., and S. Gatt, "Sphingomyelin: metabolism, chemical synthesis, chemical and physical properties," Chapter 4 from *Phospholipids* (Hawthorne, J.N., and G.B. Ansell, eds., Elsevier Biomedical Press, Amsterdam, 1982, pp. 129–177).

Barenholz, Y. et al., "A Calorimetric Study of the Thermotropic Behavior of Aqueous Dispersions of Natural and Synthetic Sphinogomyelins," *Biochemistry* 15(11): 2441–2447 (1976).

Byers, S.O., and M. Friedman, "Transport of Cholesterol During Phosphatide–Induced Hypercholesterolemia," *Biochim. Biophys. Acta* 125: 157–165 (1966).

Byers, S.O., et al., "Mechanism Underlying Phosphatide–induced Hypercholesterolemia," *The Journal of Biological Chemistry* 237(11): 3375–3380 (1962).

Cooper, R.A., "Abnormalities of Cell–Membrane Fluidity in the Pathogenesis of Disease," *The New England Journal of Medicine* 297(7): 371–377 (1977).

(List continued on next page.)

*Primary Examiner*—Gollamudi S. Kishore
*Attorney, Agent, or Firm*—Foley & Lardner

[57] ABSTRACT

A method of improving renal function is disclosed. A suspension of small, unilamellar vesicles composed primarily of phospholipids similar in nature to those of egg phosphatidylcholine is administered parenterally to a subject in need of such improvement repeatedly and over an extended period of time of at least several days, until a significant drop in plasma creatinine concentration is observed.

6 Claims, 3 Drawing Sheets

OTHER PUBLICATIONS

Frank, A., et al., "Spontaneous Transfer of Sphingomyelin between Phospholipid Bilayers," *Biochemistry* 22: 5647–5651 (1983).

Gabizon, A., et al., "Liposomes as in Vivo Carriers of Adriamycin: Reduced Cardiac Uptake and Preserved Antitumor Activity in Mice," *Cancer Research* 42: 4734–4739 (1982).

Howard, A.N., et al., "Atherosclerosis Induced in Hypercholesterolaemic Baboons by Immunological Injury; and the Effects of Intravenous Polyunsaturated Phosphatidyl Choline," *Atherosclerosis* 14: 17–29 (1971).

Kirby, C.J., and G. Gregoriadis, "A Simple Procedure For Preparing Liposomes Capable of High Encapsulation Efficiency Under Mild Conditions," Chapter 2 from *Physiology of Membrane Fluidity*, vol. 1 (Shinitzky, M., ed., CRC Press, Inc., Florida, 1984, pp. 19–22).

Martin, F.J., and R.C. MacDonald, "Phospholipid Exchange between Bilayer Membrane Vesicles," *Biochemistry* 15(2): 321–327 (1976).

Moscona–Amir, E., et al., "Role of Lipids in Age–Related Changes in the Properties of Muscarinic Receptors in Cultured Rat Heart Myocytes," *Biochemistry* 25: 8118–8124 (1986).

Patelski, J., et al., "Modification of Enzyme Activities in Experimental Atherosclerosis in the Rabbit," *Atherosclerosis* 12: 41–53 (1970).

Stafford, W.W., and C.E. Day, "Regression of Atherosclerosis Effected By Intravenous Phospholipid," *Artery* 1(2): 106–114 (1975).

Williams, K.J., et al., "Intravenously Administered Lecithin Liposomes: A Synthetic Antiatherogenic Lipid Particle," *Perspectives in Biology and Medicine* 27(3): 417–431 (1984).

Yechiel, E., and Y. Barenholz, "Relationships between Membrane Lipid Composition and Biological Properties of Rat Myocytes," *The Journal of Biological Chemistry* 260(16): 9123–9131 (1985).

Yechiel, E., et al., "Lateral Mobility and Organization of Phospholipids and Proteins in Rat Myocyte Membranes," *The Journal of Biological Chemistry* 260(16): 9132–9136 (1985).

Williams (1986) BBA. 875 p. 183.

Williams (1984) Perspectives in Biol. & Med. 27, p. 417.

Liu (1990). BBA. 1022, p. 348.

Robins Pathologic basis of disease Saunders Comp. 1984.

METHOD OF IMPROVING RENAL FUNCTION

This application is a continuation of application Ser. No. 08/257,865, filed Jun. 10, 1994, abandoned.

FIELD OF THE INVENTION

The present invention relates to a method of improving renal function.

REFERENCES

Amselem, S., et al., *Liposome Technology*, 1993 (Gregoriadis, G., ed), p501–524, CRC Press, Boca Raton, Fla.

Barenholz, Y., et al., *Biochemistry*, 16:2806 (1977).

Barenholz, Y., et al., Liposome Technology, 1993 (Gregoriadis, G., ed), p524–607, CRC Press, Boca Raton, Fla.

Guyton, A. *Textbook of Medical Physiology, Eighth Ed.*, chapters 26–28; W. B. Saunders Co., 1991.

Harrison, T. R., editor-in-chief, *Harrison's Principles of Internal Medicine*, Twelfth Ed., p 271–279; 1131–1156, McGraw Hill, Inc., 1991.

Hertz, R., et al., *Chem Phys Lipid*, 15:138 (1975).

Levida, M. *Handbook of Nutrition in the Aged* (R. R. Watson ed.), CRC Press, pp 89–109 (1985).

Shinitsky, M., et al., *J. Biol Chem*, 249:2652 (1974).

Szoka, F., et al., *Ann Rev Biophys Bioeng*, 9:467 (1980).

BACKGROUND OF THE INVENTION

Acute renal failure (ARF) refers to a deterioration in renal function sufficient to result in the accumulation of nitrogenous wastes in the body. In general, patients suffering from acute renal injury can regain kidney function if the condition is diagnosed early and treated promptly.

Chronic renal failure, however, involves irreversible kidney damage, typically progressive and permanent destruction of nephrons. Early diagnosis and treatment of acute renal failure can in some cases arrest or prevent progression to a chronic condition.

Approximately five percent of all hospitalized patients develop acute renal failure; in some clinical settings, such as intensive care units, ARF can occur in up to 20 percent of the patients. Acute renal failure may be due to prerenal, renal or postrenal causes. About 40 to 80 percent of all cases of acute renal failure are caused by decreased renal perfusion (prerenal azotemia), often resulting from varied conditions or events such as gastrointestinal hemorrhage, burns, diarrhea, severe congestive heart failure, pancreatitis, or sepsis. Postrenal causes, such as bladder neck constriction, account for about 10 percent of all cases of ARF while renal causes include disorders such as thrombosis, emboli, and vasculitis. Additionally, two types of common pharmacologic agents, non-steroidal anti-inflammatory agents (NSAID's) and angiotensin converting enzyme inhibitors may cause ARF in predisposed patients. Cross sectional studies have also found that aging is typically accompanied by a decline in renal function (Harrison).

ARF is typically detected by determination of glomerular filtration rate (GFR) or blood urea nitrogen or serum creatinine levels. GFR is the rate of ultrafiltration of plasma across the walls of the glomerular capillaries and measurement of total GFR of both kidneys provides a sensitive index of overall renal excretory function. Normal renal excretory function is indicated by a GFR of about 125 mL/min (180 L/day), although when renal excretory capacity is impaired, total GFR declines. Often, measurements of urea and creatinine concentrations are used to assess the glomerular filtration rate. Both substances are produced at a relatively constant rate by the liver and muscles; an increase in their respective serum concentrations occurs as GFR declines due to the fact that both compounds undergo complete glomerular filtration and are not reabsorbed by the renal tubules. Creatinine provides a more reliable index of GFR than urea because urea can back diffuse more completely from tubule lumen to peritubular blood than creatinine. Thus, blood urea nitrogen levels are typically higher than serum creatinine levels; a normal ratio of blood urea nitrogen to serum creatinine is about 10.

Chemical analysis of both urine and serum samples are useful indicators of ARF. For example, the range of urine osmolalities that can be achieved by an individual with normal-functioning kidneys (40 to 1200 mosmol/kg) is much larger than the range achievable in diseased kidneys (250–350 mosmol/kg). Typically, acute renal failure is characterized by urine osmolalities of below about 400 mosmol/kg, urine sodium concentrations above about 40 mmol/L, a ratio of urine-to-plasma creatinine levels below 20, and a fractional excretion of filtered sodium, defined as the ratio of urine sodium concentration/serum sodium concentration to urine creatinine concentration/serum creatinine concentration multiplied by 100, of about 2 (Harrison).

As mentioned above, the early effective treatment of ARF can arrest the progression of the condition to chronic renal failure, where permanent kidney damage occurs.

SUMMARY OF THE INVENTION

The present invention is based on the discovery that treatment of subjects with intravenously administered liposomes of the type described herein results in a significant improvement in renal function, in a subject with diminished renal function. The effect of liposomal treatment on kidney function is evidenced by measurable changes in kidney serum creatinine levels, urine maximal osmolality and sodium concentration, as well as medullary Na-K ATPase activity.

The invention includes in one aspect, a method of improving renal function in a subject in need of such treatment, i.e., a subject having diminished or failing renal function. In the method of the invention, a suspension of liposomes composed primarily of phosphatidylcholine (PC) phospholipids is administered in an amount effective to produce, over an extended period of several dosings, a substantial improvement in overall renal function of the treated subject. The PC phospholipids have a phase-transition temperature between about −10° to 37° C., preferably a transition temperature of less than about 5° C., as exemplified by egg phosphatidylcholine (egg PC) which has a transition temperature of −5° C.

In one embodiment, the liposome suspension is administered to a patient suffering from acute renal failure in an amount effective to produce a significant lowering of elevated levels of plasma creatinine.

In another embodiment, the liposome suspension is administered to a middle aged subject suffering from age-related diminution of renal function. The liposomes are administered intravenously in an amount effective to produce, over an extended period of several dosings, a substantial improvement in overall renal capacity as determined by measurement of plasma creatinine levels. The liposomes in the composition are preferably small unilamellar vesicles (SUV's) having sizes predominantly between 0.02 and 0.08 microns.

Preferably, the liposome suspension is administered 1–3 times per week, at a dose of between about 0.05 and 1 g lipid/kg body weight.

The features and details of the invention will become more apparent and appreciated by one skilled in the art to which this invention pertains from the following detailed description of the invention.

DETAILED DESCRIPTION OF THE INVENTION

I. Preparation of Liposomes

Figure 1:
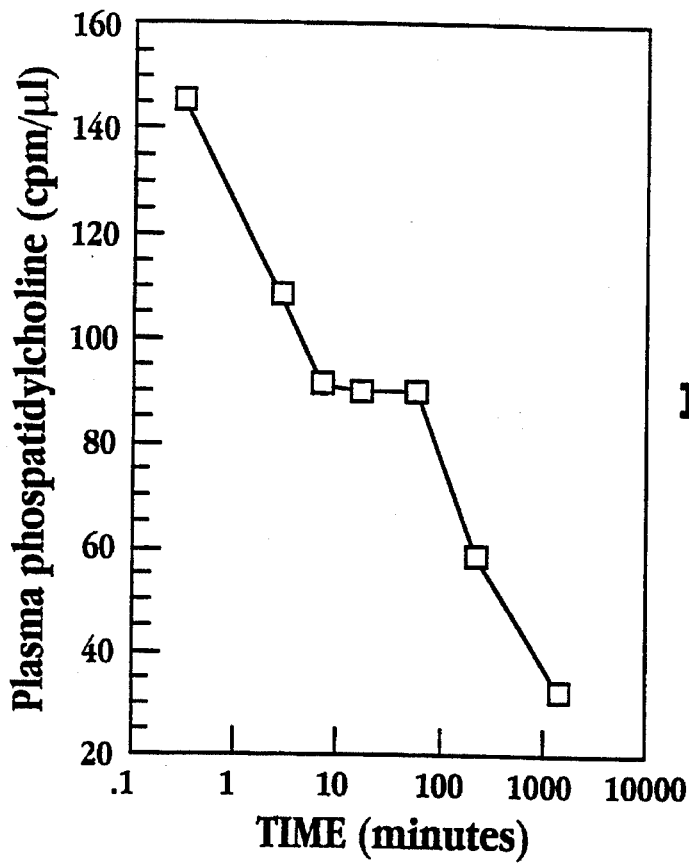
FIG. 1 illustrates the blood circulation time of intravenously administered PC SUV's in rat, measured as a function of plasma PC concentration over time.

The invention includes, in one aspect, administering to a subject (an animal or a human) a suspension of liposomes to improve renal function. The subject in need of such treatment is one suffering from acute renal failure, or loss of renal function, or age-related diminution of renal function. The treatment of acute renal failure by the method of the invention can arrest progression of the condition to chronic renal failure.

In one preferred embodiment, described and used in the examples below, the liposomes are composed predominantly (more than 50 mole percent, preferably more than 80–90 mole percent) of phosphatidylcholine (PC) having a phase transition temperature less than about 37° C., preferably between about −10° to 24° C., e.g., 5° C. or lower.

The liposome composition used in the method of the present invention is composed primarily of PC phospholipids. PC phospholipids include those phospholipids having a choline moiety and where the fatty acid chain portion of the phospholipid may vary in length and degree of unsaturation.

One preferred vesicle composition includes egg PC, which contains predominantly 1-palmitoyl, 2-oleyl PC and 1-palmitoyl,2-linoleyl PC. The liposomes may be composed entirely of the egg PC, which has a transition temperature of −5° C., or may contain other lipid components which (i) are not immunogenic, (ii) do not contribute a significant portion, i.e., more than 25–50 mole percent, of lipids with high phase transition temperature. Additional components may include negatively charged lipids, such as phosphatidylglycerol (PG) or phosphatidylserine (PS). Of course, the mole percentage of these lipids should be relatively low with respect to PC. The liposomes may also include cholesterol or other sterols, in an amount preferably less than about 40 mole percent.

Lipid protective agents, such as α-tocopherol, α-tocopherol acetate, or α-tocopherol succinate, may also be included in the lipids forming the liposomes, to protect the lipid components against free radical damage (Levida). Typically such agents are included at a mole percentage between about 0.05% and 2%. It is advantageous to add α-tocopherol to the liposomes to maintain a balance between vitamin E and polyunsaturated lipids in the liposomes.

A. Unsized Liposomes

A variety of methods for producing liposomes are available, and these have been extensively reviewed (Szoka 1980). In general these methods produce liposomes with heterogeneous sizes from about 0.02 to 10 microns or greater. As will be discussed below, liposomes which are relatively small and well defined in size are preferred for use in the present invention, hence a second processing step for reducing the size and size heterogeneity of liposomal suspensions will usually be required.

In one preferred method for forming the initial liposome suspension, the vesicle-forming lipids are taken up in a suitable organic solvent system, and dried in vacuo or under an inert gas to form a lipid film in a vessel. An aqueous suspension medium, such as a sterile saline solution, is added to the film, and the vessel is agitated until the lipids have hydrated to completion, typically within 1–2 hours. The amount of aqueous medium added is such as to produce a final liposome suspension containing preferably between about 10 and 30 g lipid per 100 ml media.

The lipids hydrate to form multilamellar vesicles (MLVs) whose sizes range between about 0.5 microns to about 10 microns or larger. In general, the size distribution of MLVs can be shifted toward slightly smaller sizes by hydrating the lipids under more vigorous shaking conditions. Example 1 describes the preparation of egg PC MLVs, prior to treating the MLVs with ultrasonic irradiation to reduce the liposome sizes.

The aqueous medium used in forming the liposomes may contain water-soluble agent(s) which enhance the stability of the liposomes upon storage. A preferred stabilizing agent is an iron-specific trihydroxamine chelating agent, such as desferrioxamine. The use of this compound in reducing lipid peroxidation and free radical damage in drug-containing liposomes has been reported in co-owned U.S. Pat. No. 4,797,285. Briefly, it was shown that the combination of a lipophilic free-radical quencher, such as α-tocopherol, and the water-soluble chelator gave substantially better protection against lipid peroxidation damage than did either protective agent alone. The chelator is included in the aqueous medium in molar excess of the amount of free iron in the medium. Typically, a chelator concentration of between about 10–200 micromolar is sufficient.

B. Sizing Liposomes

The suspension of liposomes prepared as above is preferably treated to produce a desired liposome size and size homogeneity.

The liposome suspension may be sized to achieve a distribution of vesicles in a range less than about 1 micron and preferably less than about 0.2–0.3 microns. Liposomes in this size range can be readily sterilized by filtration through a depth filter. Smaller vesicles also show less tendency to aggregate on storage, thus reducing potentially serious vascular blockage problems when the composition is administered parenterally. Finally, liposomes which have been sized down to the submicron range show more uniform biodistribution and drug clearance characteristics.

Figure 2:
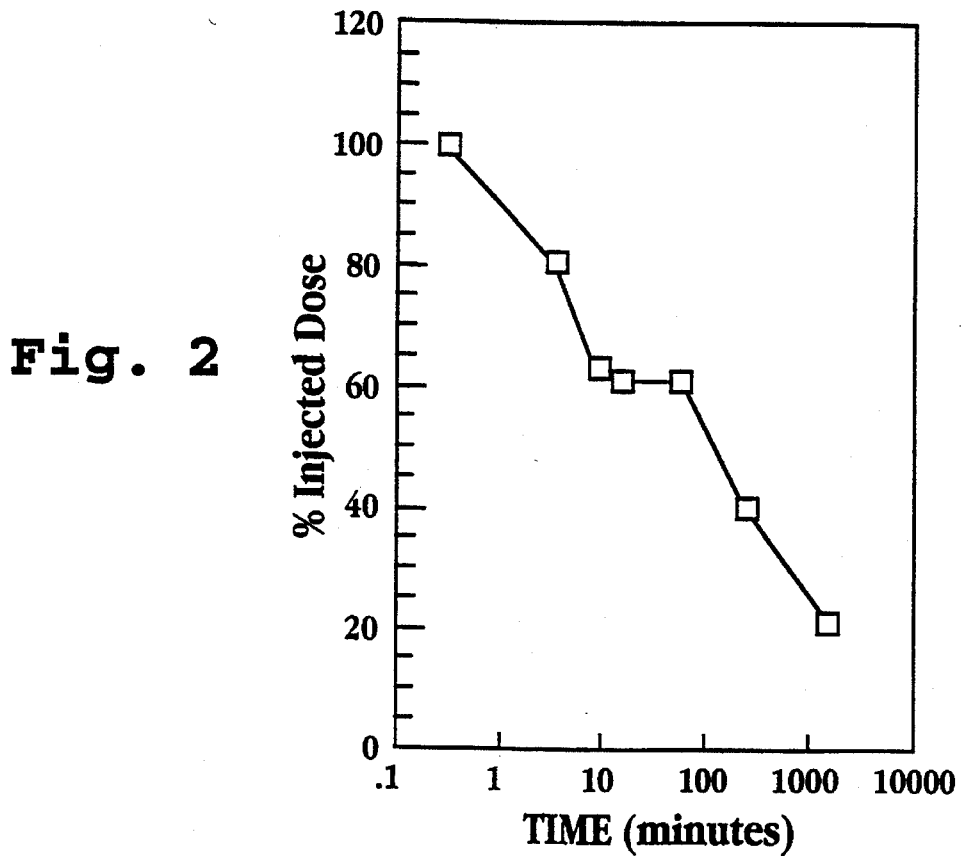
FIG. 2 illustrates the blood circulation time of intravenously administered PC SUV's in rat, measured as a function of percent injected dose over time.

Preferred liposomes are small unilammellar vesicles (SUVs), i.e., single-bilayer liposomes having sizes between about 0.02 to 0.08 microns. SUVs have relatively long blood circulation halflives, when administered intravenously. This is illustrated in FIGS. 1 and 2 which show plots of liposome retention in the bloodstream, measured up to 1,000 minutes after IV injection, and expressed either as PC measured in plasma (FIG. 1), or as percent injected dose (FIG. 2). As seen, significant amounts of liposomes remained in the bloodstream even at 1,000 minutes.

Several techniques are available for reducing the sizes and size heterogeneity of liposomes, in a manner suitable for the present invention. Ultrasonic irradiation of a liposome suspension either by bath or probe sonication produces a progressive size reduction down to SUVs. A sonicating procedure used to produce SUVs is described in Example 1. Homogenization is another method which relies on shearing energy to fragment large liposomes into smaller ones. In a typical homogenization procedure, MLVs are recirculated through a standard emulsion homogenizer until selected liposome sizes, typically less than 0.1 microns, are observed.

Extrusion of liposomes through a small-pore polycarbonate membrane is an effective method of reducing liposome size down to a relatively well-defined size distribution. An average range is between about 0.03 and 1 micron, depending on the pore size of the membrane, such as described in Example 2. Typically, the suspension is cycled through the membrane several times until the desired liposome size distribution is achieved. The liposomes may be extruded through successively smaller-pore membranes, to achieve a gradual reduction in liposome size.

The size-processed liposome suspension may be readily sterilized by passage through a sterilizing membrane having a particle discrimination size of about 0.2 microns, such as a conventional 0.22 micron depth membrane filter. If desired, the liposome suspension can be lyophilized for storage and reconstituted shortly before use.

II. Utility

A. Treating Acute Renal Failure

In one treatment method, the liposomal suspension of the present invention is administered parenterally over an extended period of time of at least several days until a significant improvement in impaired renal function is achieved, in a subject having acute renal failure. The method is used for treatment of renal failure, that is, to improve renal function by preventing progression of ARF to chronic renal failure.

Improvement in renal function is commonly indicated by plasma creatinine levels; commencement of the recovery phase of ARF occurs when the glomerular filtration rate increases so that blood urea nitrogen and serum creatinine concentrations no longer continue to rise. However, significant recovery is typically indicated by reduction in plasma creatinine levels or change in urinary osmolality.

The liposomal suspension is typically administered at a dosing frequency no greater than once per day, although dosing frequency may vary depending on the severity of the renal disorder, the age and overall general health of the subject, and other pre-existing conditions.

Additionally, and at any point in the treatment, the liposomal suspension may be administered in combination with other known agents or methods of treatment to produce the desired improvement in renal function and glomerular filtration rates and or maintenance of serum creatinine levels.

The liposomes may be conveniently administered as a series of dosages, given over a period of at least several days, and preferably maintained by continued doses at one to several month intervals over the lifetime of the treated individual. The amount of liposomes administered at each dose is between about 0.01 and 1.0 g lipid per kg of body weight, and preferably between about 0.05–1.0 g lipid per kg of body weight, although the dose may be substantially less. Long term dosages are typically delivered at a rate of between about 0.001–1 g lipid per kg body weight per day. In a preferred embodiment, the liposome suspension is administered 1–3 times per week, at a dose of between about 0.05 and 1 g lipid/kg body weight.

A typical dose for an 80 kg individual would be between about 40 and 80 grams lipid, corresponding to between 200 and 400 ml of an up to 20 g lipid/100 ml. Administration may be by iv (intravenous) injection, but is preferably done by iv drip over a period of at least about 1 hour, to minimize tissue and blood trauma at the site of administration. The liposomes may be suspended in sterile saline or in a nutritional or drug-containing medium, such as a glucose/salt medium, to combine liposome treatment with other parenteral therapy.

Typically, before the first dose is given, both urine and plasma samples are withdrawn and biochemical analyses performed, such as urine maximal osmolality, urine sodium concentration, and both urine and plasma concentrations of urea and creatinine, to provide a baseline for comparison over the course of liposome treatment. The liposome treatment is continued until renal function is improved as evidenced by a change in creatinine level or urine concentration.

Following the first liposome administration, plasma creatinine, and optionally other biochemical markers of renal function, are measured, and a second liposome dose is given typically between 2 and 7 days subsequent to the first dose. Further doses may likewise be given at 2–7 day intervals until either the plasma creatinine measurements no longer decrease or desired plasma creatinine concentrations are achieved. Thereafter, the subject may be maintained within the target plasma creatinine range by periodic maintenance liposome treatments, e.g., every 1–2 months.

B. Restoring Diminished Renal Function

According to another aspect of the invention, the method is useful in improving renal function in a subject who has age-related diminution of renal function and decreased GFR. In this method, the liposomal suspension is administered parenterally over an extended period of time of at least several days to a subject suffering from renal failure until a major improvement in renal function is achieved.

The liposome treatment for age-related decline in renal function was applied to laboratory animals, as described in Example 3–5. In one series of tests, three groups of Sabra male rats, aged 5 months (young), 12 months (middle age), and 22 month (old) were treated with a suspension of egg PC SUVs. The treatment consisted of 6 intravenous administrations of 1 gram SUV per 1 kg body weight over a three week period. Two months following the final SUV treatment, the function of the kidney was assessed by evaluating plasma creatinine levels, urine maximal osmolality and sodium concentration, and medullary Na-K-ATPase activity as described in Examples 3-5.

Figure 3:
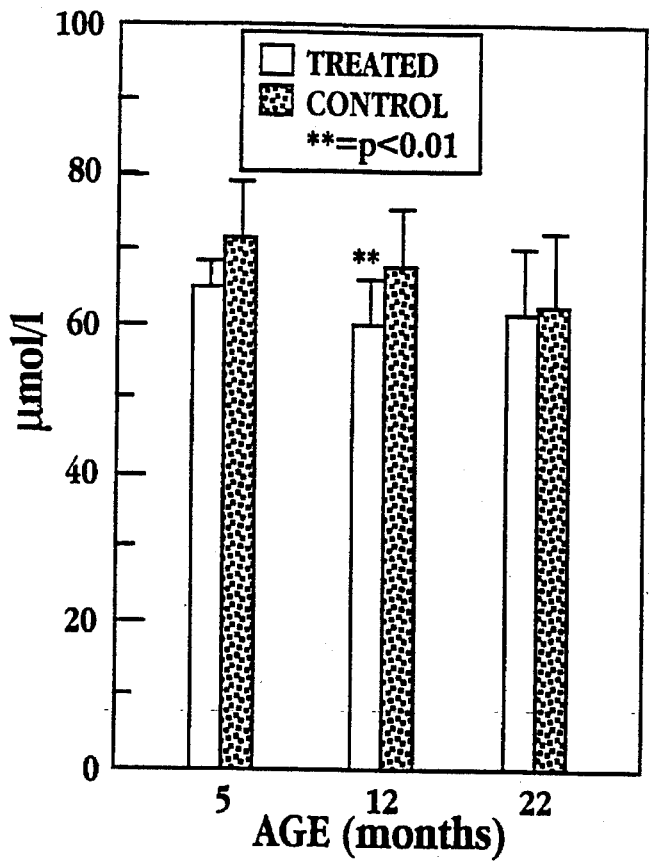
FIG. 3 is a bar graph showing the reduction in plasma creatinine concentration as a function of intravenous liposome treatment (solid bars: treated subjects; striped bars: untreated) for three age groups of male rats.

As seen in FIG. 3, a decline in plasma creatinine levels after PC SUV treatment for all three groups of animals is observed, with the most prominent lowering of plasma creatinine observed in the middle aged group (approximately 15 percent reduction in plasma creatinine). A decrease in plasma creatinine levels correlates with increased glomerular filtration rate and accordingly, enhanced renal excretory function. The animal ages given in FIGS. 3–6 refer to the ages at the start of the treatment. The actual measurements were thus made about 2.5 months after the indicated ages.

Figure 4:
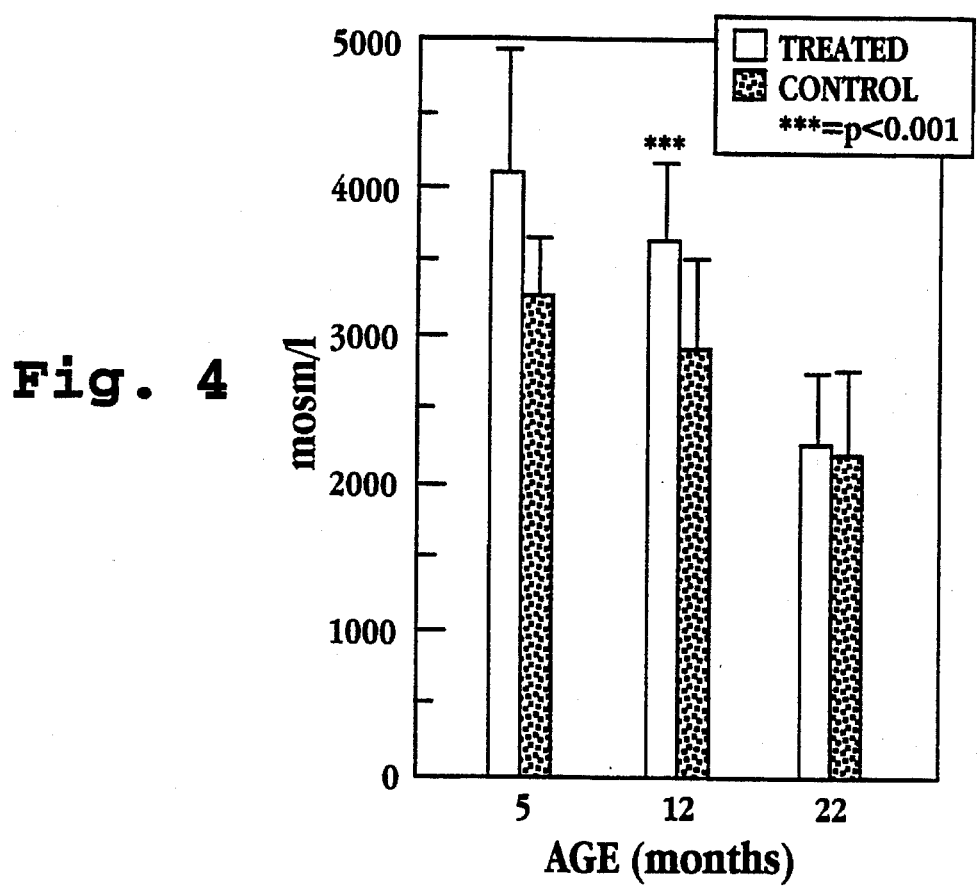
FIG. 4 is a bar graph showing the elevation of urine maximal osmolality as a function of intravenous liposome treatment (solid bars: treated subjects; striped bars: untreated) for three age groups of male rats.

An improvement in the ability to concentrate urine following liposomal treatment was also observed, as shown in FIG. 4. The limited ability to concentrate urine is a common indication of impaired renal function; significant improvement in urine maximal osmolality was seen in both the young and the middle-aged groups. The middle aged subjects showed an improvement of nearly 30% in urine concentrating capacity.

Figure 5:
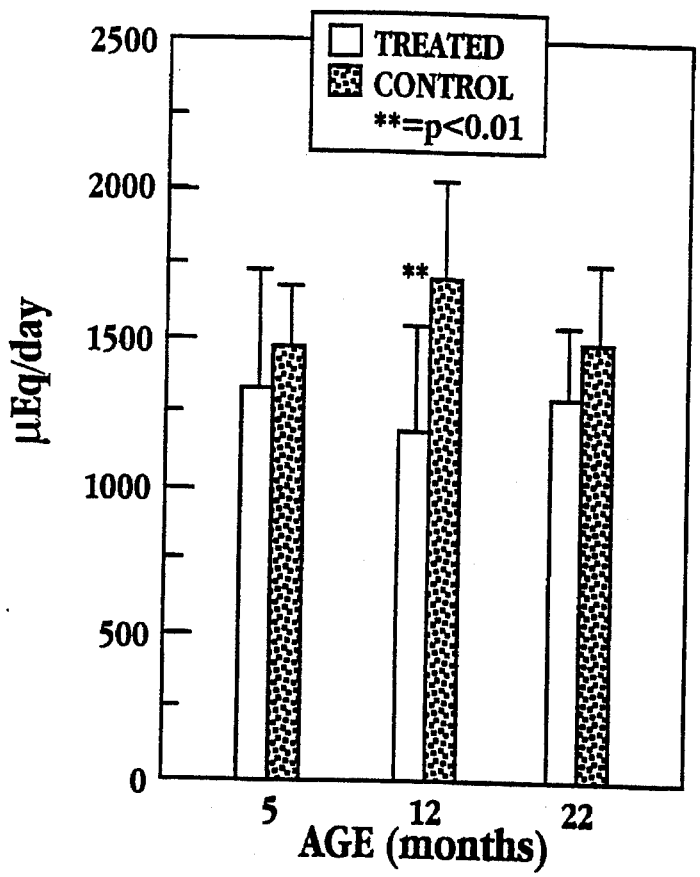
FIG. 5 shows the reduction in sodium excretion as a function of intravenous liposome treatment (solid bars: treated subjects; striped bars: untreated) for three age groups of male rats.
Figure 6:
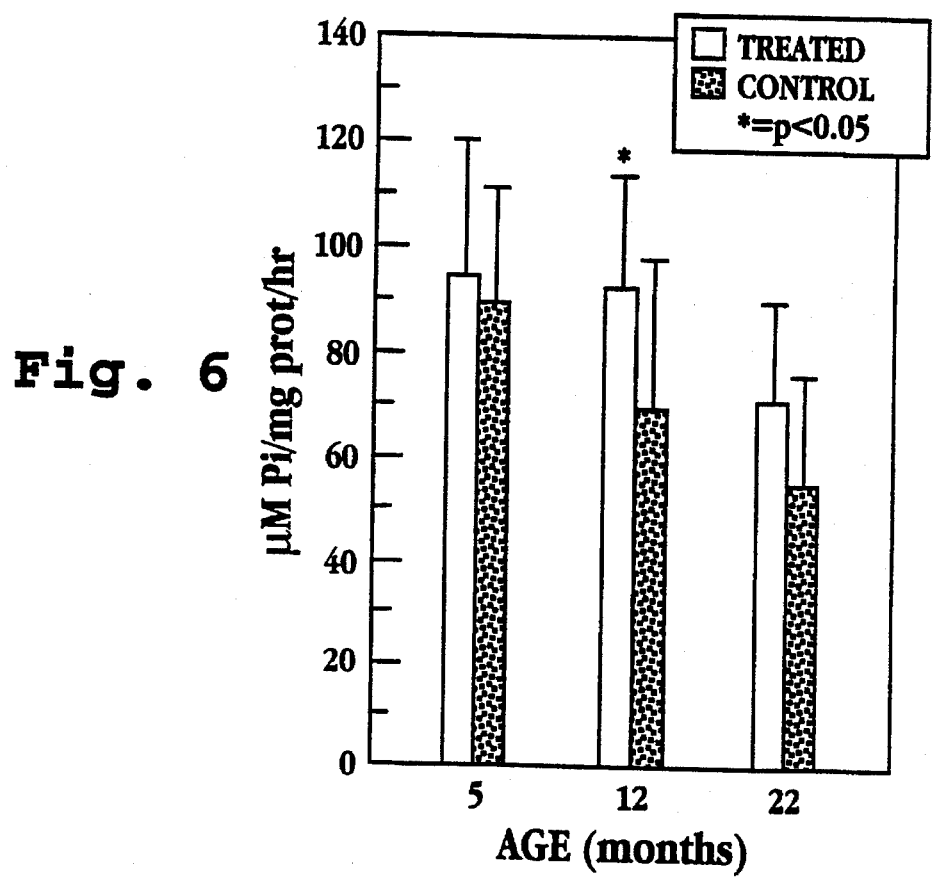
FIG. 6 illustrates enhanced renal medullary Na-K-ATPase activity as a function of intravenous liposome treatment (solid bars: treated subjects; striped bars: untreated) for three age groups of male rats.

Changes were also observed in the levels of sodium excretion and in renal medullary Na-K-ATPase activity upon liposome treatment, as seen in FIGS. 5 and 6, respectively. Impaired renal function is often accompanied by a suppression of fractional sodium reabsorption thus leading to an increase in fractional salt excretion. FIG. 5 shows that all three groups of treated subjects experienced an improvement in overall renal function as evidenced by reduced sodium excretion.

The above noted biochemical changes indicate improved renal function upon liposomal treatment for all three groups of treated subjects with the most significant improvement resulting for the middle-aged group.

From the foregoing, it will be appreciated how various objects and features of the invention are met. Administration of liposomes to a subject is effective in significantly lowering plasma creatinine concentrations and in improving urine osmolality, sodium excretion and renal medullary Na-K ATPase activity. These improvements are observed after only a relatively short treatment period, e.g., three weeks.

The following examples illustrate various methods for preparing liposome compositions and using the compositions in the treatment method of the invention. The examples are intended to illustrate, but in no way limit, the scope of the invention.

MATERIALS

Egg phosphatidylcholine (egg PC) recovered from egg yolk was prepared according to known methods (Shinitsky). High purity egg PC may also be purchased from Avanti Polar Lipids (Alabaster, AL) or Lipoid KG (Ludwigshafen, Germany). The egg PC was determined to be greater than 99% pure, based on thin layer chromatography (TLC) analysis. The egg PC fatty acid composition was similar to the reported composition (Hertz). The main PCs of the preparation included 1-palmitoyl,2-oleyl PC and 1-palmitoyl,2-linoleyl PC. Thin-layer chromatography plates, 0.25 silica gel HR and 0.024 silica gel, were obtained from Merck (Darmstadt, Germany) and Analtech (Newark, Del.), respectively.

EXAMPLE 1

Preparation of Small Unilamellar Vesicles: Sonication

Egg PC dissolved in chloroform was placed in a 100 ml vessel and dried to a thin film under nitrogen. Sterile saline was added to the lipid film to a final concentration of about 100 mg/ml, and the lipid film was hydrated with swirling. The resulting multilamellar vesicle (MLV) suspension was then bath sonicated for 1 hour using a Heat System Sonicator, Model 375W, at a power setting of 40–50% full value. The temperature of the suspension was maintained at about 4° C. under nitrogen during sonication. The sonicated suspension was separated from large vesicles by ultracentrifugation at 100,000 g for 1 hour (Barenholz, 1977). The suspension of SUVs, having a concentration of about 100 mg/ml, was filter sterilized.

EXAMPLE 2

Preparation of Small Unilamellar Vesicles: Extrusion

Homogeneous small unilamellar vesicles of egg PC with an average diameter of 39±8 nm, in 0.15M NaCl were prepared by extrusion using serial filtration through polycarbonate filters in a GH 76–400 pressure cell (Nucleopore) (Amselem et al, 1993). Liposomal size was determined using a Coulter model N4 sub-micron particle analyzer equipped with a size distribution processor analyzer (Barenholz et al, 1993). The final extrusion step was through a 0.05 micrometer pore polycarbonate filter. Egg PC SUV's were sterilized by filtration through sterile 0.22 micrometer Milipore filters.

EXAMPLE 3

Effect of Egg PC SUV Treatment on Plasma Levels of Creatinine

The serum creatinine levels in three groups of Sabra male rats aged 5 months (young), 12 months (middle age), and 22 months (old) following liposome treatment were examined to provide a measure of kidney function. Egg PC SUV's were prepared as described in Examples 1 and 2. The young group consisted of 5 treated rats and 6 controls, the middle aged group consisted of 12 treated rats and 12 controls, and the old group consisted of 10 treated rats and 14 controls. The rats were injected through the femoral vein with either sterile saline (controls) or with a suspension of egg PC SUV's. The animals were treated with 6 i.v. administrations of 1 gram SUV lipid per 1 kg subject body weight over a 3 week period. After two months, the function of the kidney was assessed by examining plasma creatinine levels. Blood samples from the three groups of animals were centrifuged at low speed to remove blood cells and the resulting serum fractions were assayed for creatinine using standard procedures. The plasma creatinine data are shown in Table I below and in FIG. 3. Plasma creatinine is expressed in units of µmol creatinine per liter of plasma. All data represent the average of each age group.

TABLE I

| Age (months) | Plasma Creatinine Concentration (µmols/L) TREATED | Plasma Creatinine Concentration (µmols/L) UNTREATED |
| --- | --- | --- |
| 5 | 65.5 | 71.3 |
| 12 | 60.1 | 67.7 |
| 22 | 61.7 | 62.8 |

The plasma creatinine levels are reduced in all three age groups upon treatment with PC SUVs, with the most significant reduction observed in the 12 month old rats.

EXAMPLE 4

Effect of Egg PC SUV Treatment on Urine Maximal Osmolality and Sodium Excretion The effect of administration of egg PC SUV's on kidney function was assessed by examining urine content. Urine samples from the three groups of rats in Example 3 were assayed for sodium content and maximal osmolality. The results are shown in Table II and in FIGS. 4 and 5, where the urine maximal osmolality is expressed in units of mosm per liter and sodium excretion is expressed in units of microequivalents per day.

TABLE II

| Age (months) | SUV Treatment | Urine Maximal Osmolality, mosm/L | Urine Sodium Content, uEq/day |
|---|---|---|---|
| 5 | + | 4120 | 1308 |
| 5 | − | 3269 | 1461 |
| 12 | + | 3754 | 1215 |
| 12 | − | 2908 | 1686 |
| 22 | + | 2306 | 1331 |
| 22 | − | 2242 | 1437 |

The data show an improvement in the ability to concentrate urine for all three SUV-treated groups as evidenced by increased urine maximal osmolality. Significant increases were seen in both the young and middle age subjects. A decrease in sodium excretion was observed for the SUV treated groups, with a very significant decrease in sodium excretion observed for the 12 month old rats.

EXAMPLE 5

Effect of Egg PC SUV Treatment on Renal Medullary Na-K ATPase Activity

The effect of administration of egg PC SUV's on kidney function was assessed by examining Na-K ATPase activity in the rats from Example 3. The Na-K-ATPase activity in the red outer medulla was colorimetrically defined as the difference between the inorganic phosphate liberated in both the presence and absence of ouabain, corrected for nonenzymatic breakdown of ATP. The reaction was initiated by addition of ATP and terminated by addition of an ammonium molybdate solution. The results are summarized in Table III and shown in FIG. 6, where Na-K-ATPase activity is reported in units of ($\mu$mol $P_i$/mg protein)/hour. The results demonstrate that medullary Na-K-ATPase activity is elevated by PC SUV treatment for all three groups of rats, most significantly for the 12 month old rats.

TABLE III

| Age (months) | Na—K—ATPase Activity ($\mu$mol $P_i$/mg protein)/hour TREATED | Na—K—ATPase Activity ($\mu$mol $P_i$/mg protein)/hour UNTREATED |
|---|---|---|
| 5 | 96.7 | 90.1 |
| 12 | 91.2 | 68.6 |
| 22 | 62.8 | 53.6 |

While various embodiments of the invention have been described herein, it will be apparent that various modifications can be made without departing from the intended scope of the invention.

It is claimed:

1. A method for improving age-related diminution of renal function in a middle-aged human subject in need of such a treatment, as evidenced by a subnormal rate of glomerular filtration of less than 180 liters per day, comprising:

intravenously administering to the subject, a suspension of small unilamellar liposomes composed of greater than 80 mole percent phosphatidylcholine phospholipids having phase transition temperatures between −10° and 37° C., said liposomes acting as the therapeutic agent for said improving, wherein the liposomes in the suspension have sizes of less than about 0.2 micron, and repeating said administering over a period of at least several days and in an amount of liposomes effective to produce an improvement in the glomerular filtration rate in said subject characterized by a reduction in serum creatinine concentration of at least 10 percent, such that said liposome suspension is administered 1–3 times per week at a dose of between about 0.05 and 1 g lipid/kg body weight.

2. The method of claim 1, wherein the liposomes in the suspension have sizes between 0.02 and 0.08 microns.

3. The method of claim 1, wherein the liposomes in the suspension are composed of egg phosphatidylcholine.

4. The method of claim 1, wherein said phospholipids have phase transition temperatures less than 5° C.

5. The method of claim 1, for use in preventing chronic renal failure in a subject suffering from acute renal failure, said acute renal failure evidenced by a ratio of urine-to-plasma creatinine concentration below 20, wherein said repeating is further effective, over said period, to improve the ratio of urine-to-plasma creatinine concentration above 20.

6. The method of claim 1, for use in improving age-related diminution of renal function in a middle-aged subject, wherein said repeating is further effective, over said period, to produce an improvement in urine concentrating capacity characterized by an increase of at least 10 percent in urine maximal osmolality.

* * * * *